US012702867B2

(12) United States Patent
Pizaine et al.

(10) Patent No.: US 12,702,867 B2
(45) Date of Patent: Aug. 11, 2026

(54) SELECTION OF MAGNETIC RESONANCE IMAGING ACQUISITIONS FOR RADIATION THERAPY PLANNING

(71) Applicant: KONINKLIJKE PHILIPS N.V., Eindhoven (NL)

(72) Inventors: Guillaume Julien Joseph Pizaine, Sartrouville (FR); Alexandre Jean Michel Popoff, Paris (FR)

(73) Assignee: Koninklijke Philips N.V., Einhoven (NL)

( * ) Notice: Subject to any disclaimer, the term of this patent is extended or adjusted under 35 U.S.C. 154(b) by 366 days.

(21) Appl. No.: 18/683,267

(22) PCT Filed: Aug. 12, 2022

(86) PCT No.: PCT/EP2022/072625
§ 371 (c)(1),
(2) Date: Feb. 13, 2024

(87) PCT Pub. No.: WO2023/020948
PCT Pub. Date: Feb. 23, 2023

(65) Prior Publication Data

US 2026/0158295 A1 Jun. 11, 2026

(30) Foreign Application Priority Data

Aug. 17, 2021 (EP) .................................... 21191610

(51) Int. Cl.
*A61N 5/00* (2006.01)
*A61N 5/10* (2006.01)

(52) U.S. Cl.
CPC ................................. *A61N 5/1039* (2013.01)

(58) Field of Classification Search
CPC .................................................. A61N 5/1039
See application file for complete search history.

(56) References Cited

U.S. PATENT DOCUMENTS

2017/0021195 A1* 1/2017 Schweizer ......... G01R 33/4808

FOREIGN PATENT DOCUMENTS

WO 2012063158 A1 5/2012

OTHER PUBLICATIONS

International Search Report and Written Opinion from PCT/EP2022/072625 mailed Nov. 17, 2022.

* cited by examiner

*Primary Examiner* — Dani Fox

(57) ABSTRACT

Disclose herein is a medical system (200, 400) where the execution of the machine executable instructions causes the computational system to: receive (300) one or more planning magnetic resonance images (106); receive (302) a radio therapy planning map from the analysis algorithm as output in response to inputting the one or more planning magnetic resonance images into an analysis algorithm (100); receive (304) the at least one metric map as output from an assessment algorithm (102) in response to inputting the output of the radio therapy planning map into the assessment algorithm; and receive (306) a pulse sequence selection (222) or a stop acquisition command (224) as output from the recommender algorithm in response to inputting the one or more planning magnetic resonance images, the output of the analysis algorithm, and the output of the assessment algorithm.

15 Claims, 5 Drawing Sheets

Fig. 1

SELECTION OF MAGNETIC RESONANCE IMAGING ACQUISITIONS FOR RADIATION THERAPY PLANNING

CROSS REFERENCE TO RELATED APPLICATIONS

This application is a U.S. national phase application of International Application No. PCT/EP2022/072625 filed on Aug. 12, 2022, which claims the benefit of EP Application Ser. No. 21/191,610.1 filed on Aug. 17, 2021 and is incorporated herein by reference.

FIELD OF THE INVENTION

The invention relates to magnetic resonance imaging, in particular to magnetic resonance imaging for radiation therapy planning.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field or the main magnetic field. Various quantities or properties of the subject can be measured spatially using MRI. Typically, MRI is used to image soft tissues that contain water or lipids.

European patent publication EP 2637745 A1 discloses a therapeutic apparatus comprising: a radio therapy apparatus for treating a target zone of a subject, wherein the radio therapy apparatus comprises a radio therapy source for generating electromagnetic radiation, wherein the radio therapy apparatus is adapted for rotating the radio therapy source about a rotational point; a mechanical actuator for supporting the radio therapy apparatus and for moving the position and/or orientation of the rotational point; and a magnetic resonance imaging system for acquiring k-space data from an imaging zone, wherein the target zone is within the imaging zone, wherein the magnetic resonance imaging system comprises a magnet for generating a magnetic field within the imaging zone, wherein the radio therapy source is adapted for rotating at least partially about the magnet.

SUMMARY OF THE INVENTION

The invention provides for a medical system, a computer program, and a method in the independent claims. Embodiments are given in the dependent claims.

A difficulty in using magnetic resonance imaging for radiation therapy planning is that it takes a great deal of experience and training to determine how many contrasts (magnetic resonance images with different acquisition parameters) are needed to accurately perform radiation therapy planning. Embodiments may provide for a means of determining the proper number of acquisitions as magnetic resonance images are being acquired. An analysis algorithm is used to produce a radiotherapy planning map using one or more planning magnetic resonance images that have been acquired. An assessment algorithm provides at least one metric map descriptive of the radiotherapy planning map. A metric map as used herein encompasses a matrix of one or more numerical values where each element of the matrix corresponds to a pixel or voxel of an image. In this case the metric map provides a pixel or voxel wise ranking or numerical measure of each pixel or voxel of the metric map.

The outputs of the analysis algorithm, the assessment algorithm, as well as the one or more planning magnetic resonance images are input into a recommender algorithm. The recommender algorithm either issues a stop command which halts the acquisition of more planning magnetic resonance images or it provides a pulse sequence selection which may be used to perform another acquisition of an additional planning magnetic resonance image. This has the advantage that acquisition of magnetic resonance images for planning may be halted once the radiotherapy planning map is sufficient for planning. This may reduce the amount of time that the magnetic resonance imaging system is used per subject.

In one aspect the invention provides for a medical system that comprises a memory storing machine-executable instructions. The memory further stores an analysis algorithm, an assessment algorithm, and a recommender algorithm. The analysis algorithm is configured to output a radiotherapy planning map in response to receiving the one or more planning magnetic resonance images descriptive of a region of interest of a subject. The radiotherapy planning map as used herein encompasses a spatially dependent mapping that is useful in planning a radiotherapy session or eradiation. The radiotherapy planning map may then have several different interpretations. It could for example be a segmentation of different images, identification of tumor or other abnormal tissue within the region of interest. The radiotherapy planning map could also be a synthetic computed tomography scan or other mapping or data which would be useful in planning radiotherapy.

The assessment algorithm is configured to output at least one metric map descriptive of the radiotherapy planning map within the region of interest in response to receiving the output of the analysis algorithm. In this example the output of the analysis algorithm is the radiotherapy planning map. However, the analysis algorithm could also output other data or information and these may be included in the data that is input into the assessment algorithm. The at least one metric map is a numerical value or values which are assigned to rank and provide a quality or confidence score in the radiotherapy planning map on a per pixel or voxel basis. The assessment algorithm may use different types of analysis depending upon what the radiotherapy planning map is.

The recommender algorithm is configured to output either a pulse sequence selection or a stop acquisition command in response to receiving the one or more planning magnetic resonance images, the output of the analysis algorithm, and the output of the assessment algorithm as input. The output of the assessment algorithm is the at least one metric map. The assessment algorithm in some examples may however output additional data which is also input into the recommender algorithm. The pulse sequence selection is a planning magnetic resonance imaging pulse sequence selection and a selection or ranking of a predetermined set of radiation therapy planning pulse sequence commands. The radiation therapy pulse sequence commands are pulse sequence commands which are used to acquire k-space data which is useful in constructing the radiotherapy planning map. These three algorithms work together and provide a decision to stop acquiring additional k-space data or to choose an additional sequence selection that can be used to acquire more k-space data.

The analysis algorithm, the assessment algorithm, and the recommender algorithm can be constructed using analytical functions or they can be constructed using artificial intelligence and be trained. As an example, if the analysis algorithm outputs the radiotherapy planning map as a pseudo- CT-scan and/or a segmentation there are analytical and artificial intelligence means of both doing this.

The medical system further comprises a computational system that may be configured for controlling the medical system. Execution of the machine-executable instructions causes the computational system to receive the one or more planning magnetic resonance images. These for example may be received by controlling the magnetic resonance imaging system to acquire the one or more planning magnetic resonance images. In other examples, they may be retrieved from a storage device or retrieved via a network interface.

Execution of the machine-executable instructions further causes the computational system to receive the radiotherapy planning map from the analysis algorithm as output in response to inputting the one or more planning magnetic resonance images into the analysis algorithm. Execution of the machine-executable instructions further causes the computational system to receive the at least one metric map as output from the assessment algorithm in response to inputting the output of the radiotherapy planning map into the assessment algorithm. Execution of the machine-executable instructions further causes the computational system to receive the pulse sequence selection or the stop acquisition command as output from the recommender algorithm in response to inputting the one or more planning magnetic resonance images, the output of the analysis algorithm, and the output of the assessment algorithm.

This embodiment may be beneficial because it may provide for an effective means of retrofitting a magnetic resonance imaging system or providing additional control functionality remotely to acquire magnetic resonance images and k-space data radiation therapy planning in an efficient means. Once the one or more planning magnetic resonance images are sufficient, then the system may stop and radiation therapy planning can commence. The use of the medical system reduces the chances that time will be wasted by acquiring more magnetic resonance images than are necessary for effective planning.

The recommender algorithm is further configured to receive at least one additional tomographic medical image descriptive of the region of interest for the subject as input. Execution of the machine-executable instructions causes the computational system to additionally input the at least one additional tomographic medical image into the recommender algorithm. The at least one additional tomographic medical image may for example be prior magnetic resonance images, CT-scans or other data and may be used to augment the generation of the radiotherapy planning map. This embodiment may be beneficial because it may provide for an improved means of generating the radiotherapy planning map.

In another embodiment the assessment algorithm is further configured to receive the one or more planning magnetic resonance images and/or receive at least one further tomographic medical image descriptive of the region of interest of the subject as input. Execution of the machine-executable instructions further causes the computational system to additionally input the one or more planning magnetic resonance images and/or the at least one further tomographic medical image into the assessment algorithm. This embodiment may be beneficial because more information is provided to the assessment algorithm to determine the at least one metric map.

In another embodiment the analysis algorithm is further configured to receive at least one supplementary tomographic medical image descriptive of the region of interest of the subject as input. Execution of the machine-executable instructions causes the computational system to additionally input the at least one supplementary tomographic medical image into the analysis algorithm. This for example may provide for a more accurate operation of the analysis algorithm. In a concrete example, if the analysis algorithm is producing segmentations of locations of organs, then the additional information provided by the at least one supplementary tomographic medical image may improve the quality of the segmentations.

In another embodiment the at least one supplementary tomographic medical image and/or the further tomographic medical image and/or the at least one additional tomographic medical image are identical. For example, they may be identical images or drawn from the same source.

In another embodiment the analysis algorithm is configured to receive up to a predetermined maximum number of planning magnetic resonance images. The analysis algorithm is configured to receive the one or more planning magnetic resonance images because the input of the analysis algorithm comprises a separate input channel for each of the planning magnetic resonance images. For example, when the analysis algorithm is a neural network the neural network can be scaled to receive multiple of the same entry. A good example from this is taking a neural network that is designed for working with grayscale images. The inputs can be tripled and these additional channels can be used for each channel of a color image. Likewise, the number of channels can be multiplied to account for the input of multiple images.

In another embodiment the analysis algorithm is configured such that the analysis algorithm comprises an image processing algorithm configured for receiving each of the predetermined maximum number of planning magnetic resonance images individually and in response, they each output an intermediate radiotherapy planning map. The analysis algorithm further comprises an image merging algorithm configured for receiving the intermediate radiotherapy planning map of each image processing algorithm and in response outputting the radiotherapy planning map. This may be an effective means of enabling an arbitrary number of inputs or the predetermined maximum number of planning magnetic resonance images. For example, the image processing algorithm may be a standard or known algorithm for segmenting images. The merging algorithm may take several different forms, for example, it may be a neural network trained to combine images, in another example, the image merging algorithm may produce an average value for each of the intermediate radiotherapy planning map. This embodiment may be beneficial because it may provide for an effective means of being able to accept a relatively large number of planning magnetic resonance images.

In another embodiment the analysis algorithm and the assessment algorithm are implemented as a single algorithm. That is to say that the at least two algorithms could be combined. For example, if the analysis algorithm and the assessment algorithm were implemented as neural networks they could be replaced with a single neural network.

In another embodiment the radiotherapy planning map comprises an organ segmentation.

In another embodiment the radiotherapy planning map comprises an identification of abnormal anatomical structures.

In another embodiment the radiotherapy planning map comprises a tumor segmentation.

In another embodiment the radiotherapy planning map comprises a pseudo computed tomography image.

In another embodiment the radiotherapy planning map comprises an electron density map.

In another embodiment the radiotherapy planning map comprises a radiotherapy dose plan.

In the above-mentioned organ segmentation, identification of abnormal anatomical structures, the identification of a tumor segmentation, the pseudo computed tomography image, the electron density map and the radiotherapy dose plan; these could be for the region of interest.

In another embodiment the analysis algorithm is a region growing algorithm.

In another embodiment the analysis algorithm is a deformable shape model. The deformable shape model has a defined shape for a particular segmentation and stretching or modifying this shape model causes an elastic deformation. Deformable shape models are very effective at performing effective segmentations.

In another embodiment the analysis algorithm is a trained neural network.

In another embodiment the analysis algorithm is a trained random forest.

In another embodiment the analysis algorithm is a registration algorithm configured to register the one or more planning magnetic resonance images to an anatomical atlas. In the case of the trained neural network and the trained random forest standard methods of training a neural network for segmentation may be used. For example, the trained neural network may be a so-called U-Net neural network.

In another embodiment the assessment algorithm is a Monte Carlo simulation configured for predicting the stability of the radiotherapy planning map.

In another embodiment the assessment algorithm is a model configured to measure a correlation in comparison with a saliency map.

In another embodiment the assessment algorithm is a principal component analysis model.

In another embodiment the assessment algorithm is an algorithm configured to measure a distance to an average model. For example, if it is a segmentation the algorithm may measure a distance or similarity to a segmentation or average model taken from a dictionary or known anatomical structure.

In another embodiment the assessment algorithm is a fitness to a statistical appearance model such as a texture analysis or a reconstruction from an archived model or anatomical atlas.

In another embodiment the recommender algorithm is a decision tree algorithm.

In another embodiment the recommender algorithm is a trained recommender neural network.

In another embodiment the recommender algorithm is a trained random forest algorithm.

The trained recommender neural network and the trained random forest algorithm may be trained by taking data that was decided by an expert and making training data.

In another embodiment the medical system further comprises a magnetic resonance imaging system. The memory further contains the predetermined set of radiation therapy planning pulse sequence commands. The predetermined set of radiation therapy planning pulse sequence commands comprises initial pulse sequence commands. Execution of the machine-executable instructions further causes the computational system to acquire initial k-space by controlling the magnetic resonance imaging system with the initial pulse sequence commands.

Execution of the machine-executable instructions further causes the computational system to reconstruct an initial planning magnetic resonance image from the initial k-space data. The initial planning magnetic resonance image is added to the one or more planning magnetic resonance images. Execution of the machine-executable instructions further causes the computational system to repeatedly perform the following steps until the stop command is received. These steps include receiving the radiotherapy planning map from the analysis algorithm as output in response to inputting the one or more planning magnetic resonance images into an analysis algorithm. These steps further comprise receiving the at least one metric map as output from the assessment algorithm in response to inputting the output of the radiotherapy planning map into the assessment algorithm.

These steps further comprise receiving the pulse sequence selection or the stop acquisition command as output from the recommender algorithm in response to inputting the one or more planning magnetic resonance images, the output of the analysis algorithm, and the output of the assessment algorithm. Naturally if a stop acquisition command is received, then the execution of these steps stops. These steps further comprise selecting subsequent pulse sequence commands from the predetermined set of radiation therapy planning pulse sequence commands using the pulse sequence selection. These steps further comprise acquiring subsequent k-space data by controlling the magnetic resonance imaging system with the subsequent pulse sequence commands. These steps further comprise constructing the subsequent planning magnetic resonance images from the subsequent k-space data. The subsequent planning magnetic resonance image is added to the one or more planning magnetic resonance images.

This embodiment may be beneficial because it may automatically stop when there is a sufficient number of magnetic resonance images to accurately perform radiation therapy planning.

In another embodiment the memory further contains a radiotherapy planning module configured to generate radiotherapy control commands in response to receiving the radiotherapy planning map. Execution of the machine-executable instructions further causes the computational system to receive the radiotherapy control commands from the radiotherapy planning module in response to inputting the radiotherapy planning map into the radiotherapy planning module. The radiotherapy planning module as used herein is a software module that generates the actual commands for controlling the radiotherapy treatment system. They for example may take a treatment plan from a physician and then take the anatomical data contained in the radiotherapy planning module to configure the commands for performing the actual eradiation of a target zone.

This embodiment may be beneficial because the radiotherapy planning map is efficiently attained with a sufficient level of quality for performing the planning of the radiation therapy.

In another embodiment the radiotherapy planning schedule is further configured to receive a planning computed tomography image descriptive of the region of interest of the subject and the radiotherapy planning map as input. The planning computed tomography image is a measured computed tomography image or a pseudo computed tomography image. For example, in some instances the pseudo computed tomography image may be derived from the one or more planning magnetic resonance images. Execution of the machine-executable instructions further causes the computational system to receive the radiotherapy control commands from the radiotherapy planning module in response to inputting the radiotherapy planning map and the planning computed tomography image into the radiotherapy planning module. This embodiment may be beneficial because it may provide for improved control of the radiotherapy treatment system.

In another embodiment the medical system further comprises the radiotherapy treatment system. The radiotherapy treatment system is configured for being controlled by the radiotherapy control commands to control irradiation of a target zone within the subject. Execution of the machine-executable instructions further causes the computational system to irradiate the target zone by controlling the radiotherapy treatment system with the radiotherapy control commands. This embodiment may be beneficial because the use of the radiotherapy planning map may have provided for improved control of the radiotherapy treatment system; the radiation therapy may be more accurate.

In another aspect the invention provides for a method of operating a medical system. The method comprises receiving one or more planning magnetic resonance images descriptive of a region of interest of a subject. The method further comprises receiving a radiotherapy planning map from an analysis algorithm as output in response to inputting the one or more planning magnetic resonance images into the analysis algorithm. The analysis algorithm is configured to output the radiotherapy planning map in response to receiving the one or more planning magnetic resonance images descriptive of the region of interest of the subject.

The method further comprises receiving at least one metric map as output from an assessment algorithm in response to inputting the output of the radiotherapy planning map into the assessment algorithm. The assessment algorithm is configured to output the at least one metric map descriptive of the radiotherapy planning map within the region of interest in response to receiving the output of the analysis algorithm.

The method further comprises receiving a pulse sequence selection or a stop acquisition command as output from a recommender algorithm in response to inputting the one or more planning magnetic resonance images, the output of the analysis algorithm, and the output of the assessment algorithm. The recommender algorithm is configured to output either the pulse sequence selection or the stop acquisition command in response to receiving the one or more planning magnetic resonance images, the output of the analysis algorithm, and the output of the assessment algorithm as input. The pulse sequence selection is a selection or a ranking of a predetermined set of radiation therapy planning pulse sequence commands.

In another aspect the invention provides for a computer program comprising machine-executable instructions, an analysis algorithm, and an assessment algorithm, and a recommender algorithm. The analysis algorithm is configured to output a radiotherapy planning map in response to receiving one or more planning magnetic resonance images descriptive of a region of interest of a subject. The assessment algorithm is configured to output at least one metric map descriptive of the radiotherapy planning map within the region of interest in response to receiving the output of the analysis algorithm. The recommender algorithm is configured to output either a pulse sequence selection or a stop acquisition command in response to receiving the one or more planning magnetic resonance images, the output of the analysis algorithm, and the output of the assessment algorithm as input. The pulse sequence selection is a selection or ranking of a predetermined set of radiation therapy planning pulse sequence commands.

Execution of the machine-executable instructions causes the computational system to receive the one or more planning magnetic resonance images. Execution of the machine-executable instructions further causes the computational system to receive the radiotherapy planning map from the analysis algorithm as output in response to inputting the one or more planning magnetic resonance images into the analysis algorithm. Execution of the machine-executable instructions further causes the computational system to receive the at least one metric map as output from the assessment algorithm in response to inputting the output of the radiotherapy planning map into the assessment algorithm. Execution of the machine-executable instructions further causes the computational system to receive the pulse sequence selection or the stop acquisition command as output from the recommender algorithm in response to inputting the one or more planning magnetic resonance images, the output of the analysis algorithm, and the output of the assessment algorithm.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor or computational system of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the computational system of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the computational system. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a computational system. 'Computer storage' or 'storage' is a further example of a computer-readable storage medium. Computer storage is any non-volatile computer-readable storage medium. In some embodiments computer storage may also be computer memory or vice versa.

A 'computational system' as used herein encompasses an electronic component which is able to execute a program or machine executable instruction or computer executable code. References to the computational system comprising the example of "a computational system" should be interpreted as possibly containing more than one computational system or processing core. The computational system may for instance be a multi-core processor. A computational system may also refer to a collection of computational systems within a single computer system or distributed amongst multiple computer systems. The term computational system should also be interpreted to possibly refer to a collection or network of computing devices each comprising a processor or computational systems. The machine executable code or instructions may be executed by multiple computational systems or processors that may be within the same computing device or which may even be distributed across multiple computing devices.

Machine executable instructions or computer executable code may comprise instructions or a program which causes a processor or other computational system to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly. In other instances, the machine executable instructions or computer executable code may be in the form of programming for programmable logic gate arrays.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a computational system of a general purpose computer, special purpose computer, or other programmable data processing apparatus to produce a machine, such that the instructions, which execute via the computational system of the computer or other programmable data processing apparatus, create means for implementing the functions/acts specified in the flowchart and/or block diagram block or blocks.

These machine executable instructions or computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The machine executable instructions or computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the computational system of a computer system to interact with and/or control an external computing device and/or apparatus. A hardware interface may allow a computational system to send control signals or instructions to an external computing device and/or apparatus. A hardware interface may also enable a computational system to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

K-space data is defined herein as being the recorded measurements of radio frequency signals emitted by atomic spins using the antenna of a Magnetic resonance apparatus during a magnetic resonance imaging scan or acquisition.

A Magnetic Resonance Imaging (MRI) image or MR image is defined herein as being the reconstructed two- or three-dimensional visualization of anatomic data contained within the magnetic resonance k-space data. This visualization can be performed using a computer.

BRIEF DESCRIPTION OF THE DRAWINGS

In the following preferred embodiments of the invention will be described, by way of example only, and with reference to the drawings in which:

FIG. 1 shows a flow chart which illustrates the data flow between the analysis algorithm, the assessment algorithm, and the recommender algorithm;

DETAILED DESCRIPTION OF EMBODIMENTS

Figure 2:
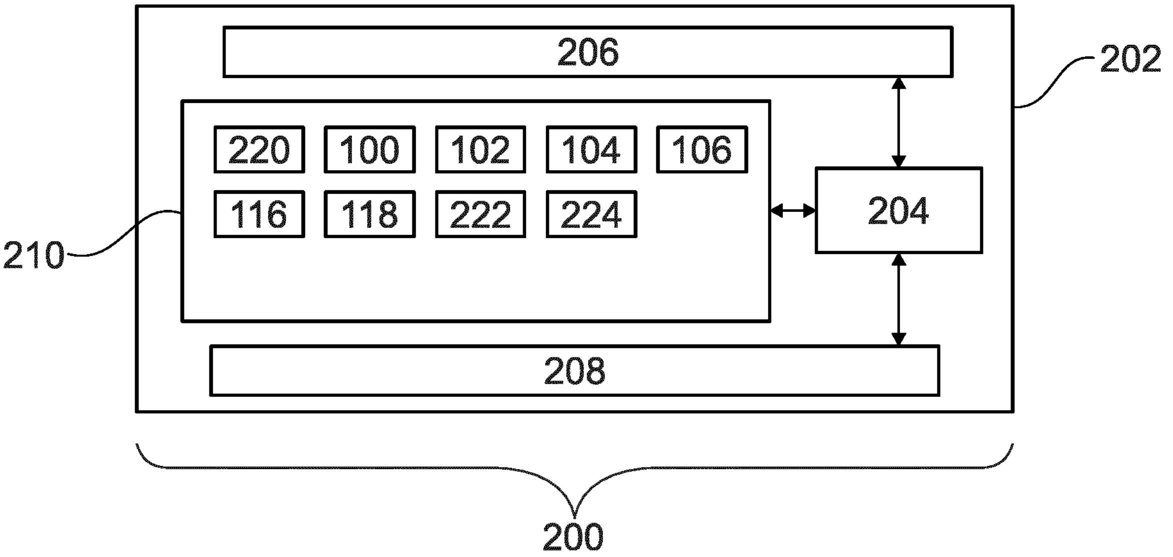
FIG. 2 illustrates an example of a medical system.

Like numbered elements in these figures are either equivalent elements or perform the same function. Elements which have been discussed previously will not necessarily be discussed in later figures if the function is equivalent.

Figure 1:
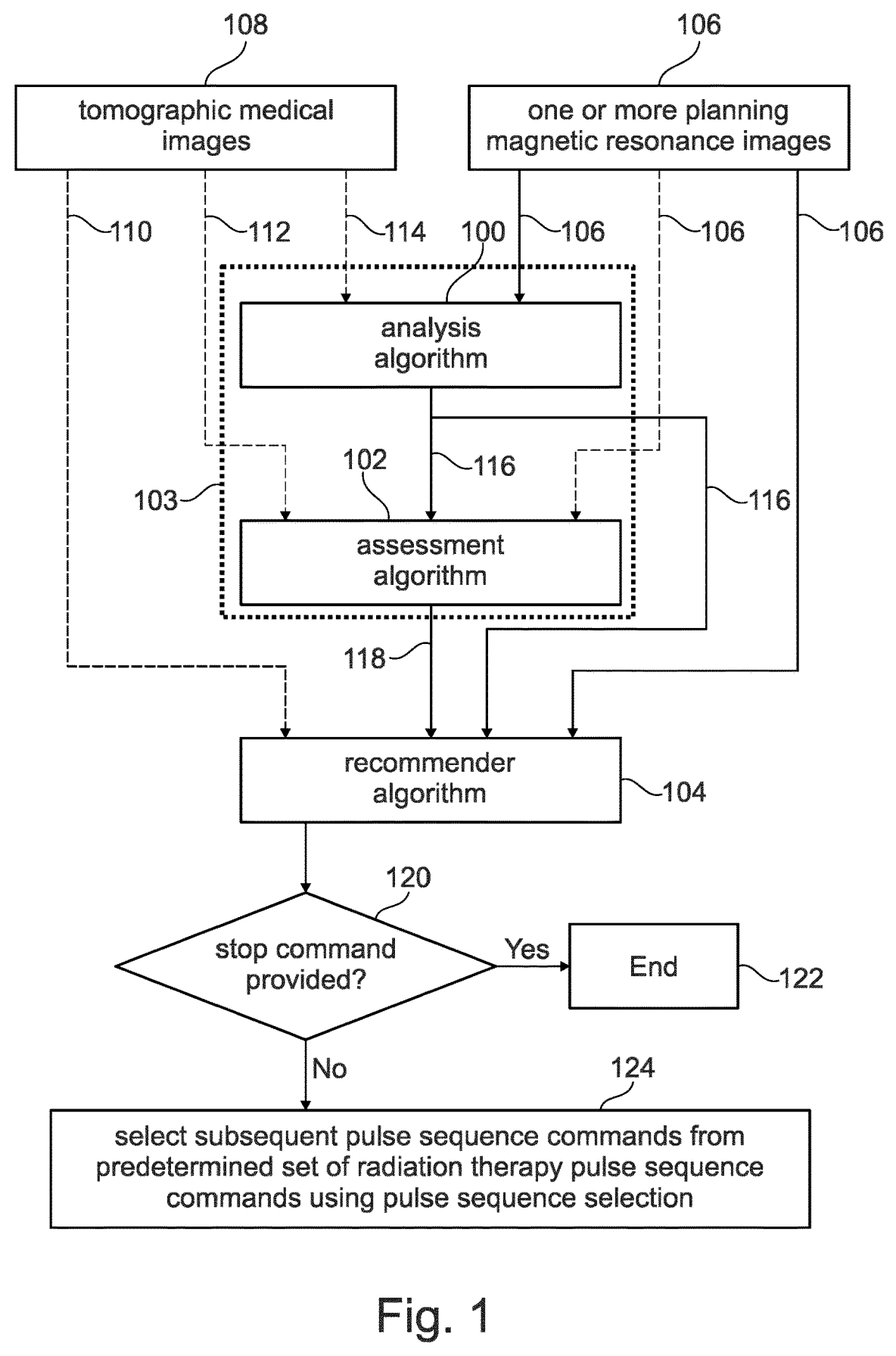

FIG. 1 illustrates the flow of data in an example algorithm. The algorithm illustrated in FIG. 1 may be added to a conventional magnetic resonance imaging system to enable it to effectively decide when to cease acquiring planning magnetic resonance images for radiation therapy planning.

There are three algorithms that work together: an analysis algorithm 100, an assessment algorithm 102, and a recommender algorithm 104. In all examples to these three algorithms one or more planning magnetic resonance images 106 are supplied. These are images of a subject for a particular region, which includes a particular region of interest. As was shown in FIG. 1 is some topographical medical images 108 which are optionally supplied to each of the algorithms, 100, 102, 104. The tomographic medical images may for example be prior acquired magnetic resonance images, computed tomography scans or other things such as segmentations or other data or historical data from the subject. The optional data is presented in the form of additional tomographic medical images 110 that are optionally supplied to the recommender algorithm.

There are additional tomographic medical images 110 that are optionally supplied into the input of the assessment algorithm 102. There are also optional supplementary tomographic medical images 114 that are optionally supplied to the analysis algorithm 100. In some cases, the additional tomographic medical images 110 may be the same as the further tomographic medical images 112 as well as being the same as the supplementary tomographic medical images 114. However, these three groups of tomographic medical images 110, 112, 114 do not need to be identical. The use of the term additional, further, and supplementary at the beginning of these tomographic medical images is simply to differentiate to provide a possibility of them being different images that are supplied to the different algorithm modules.

The analysis algorithm is shown as receiving the one or more planning magnetic resonance images 106 as input and again optionally the supplementary tomographic medical images 114. The analysis algorithm 100 in response outputs a radiotherapy planning map 116. The output of the analysis algorithm is input into the assessment algorithm 102 as well as the recommender algorithm 104.

The assessment algorithm 102 is shown as optionally receiving the further tomographic medical images 112 and also optionally receiving the one or more planning magnetic resonance images 106. In response, the assessment algorithm outputs 118 at least one metric map. The at least one metric map is descriptive of the radiotherapy planning map within the region of interest, for example it may be a rating or quality measure of the radiotherapy planning map 116. The analysis algorithm 100 and the assessment algorithm 116 may be optionally combined into a combined algorithm 103.

The recommender algorithm 104 is shown as taking the output of the assessment algorithm 118, the output of the analysis algorithm 116, and the one or more planning magnetic resonance images 106 as input. The recommender algorithm 104 is also shown as optionally receiving the additional tomographic medical images 110 as input. In response, the recommender algorithm 104 is configured to output either a stop acquisition command or a pulse sequence selection. The method then proceeds to box 120, which is a question box, if the stop command is provided then the method proceeds to box 122 and there is an end to the acquisition of planning magnetic resonance images 122.

If a stop command is not provided the method proceeds to box 124. In this case the pulse sequence for the next acquisition is selected from a predetermined set of radiation therapy pulse sequence commands using a pulse sequence selection that was output by the recommender algorithm 104. Once these pulse sequences have been selected, the magnetic resonance imaging system may be used to acquire more k-space data and acquire one or more images that are then added to the one or more planning magnetic resonance images and the method may start from box 106 again. The steps in dataflow illustrated in FIG. 1 may be easily integrated into existing magnetic resonance imaging systems. It may for example be implemented in the control system of the magnetic resonance imaging system itself or it may also be available as, for example, a remote or cloud service.

FIG. 2 illustrates an example of a medical system 200. The example illustrated in FIG. 2 could for example be incorporated into a magnetic resonance imaging system in a variety of ways. In one case it could be incorporated directly into the control system or it could be provided as an external module which is available over a network or the internet, for example as a cloud service. The medical system 200 is shown as comprising a computer 202 that has a computational system 204. The computer 202 is intended to represent one or more computing systems that may be at the same location and/or distributed. Likewise, the computational system 204 is intended to represent one or more computational systems that may be at one or more locations. The computer 202 is further shown as comprising an optional hardware interface 206 that may be connected to the computational system 204 to enable it to communicate and control other components of the medical system 200. The computational system 204 is further shown as being in communication with an optional network interface 208. The computational system 204 is also in communication with a memory 210. The memory 210 is intended to represent various types of memory and storage devices that may be in communication with the computational system 204.

The memory 210 is shown as containing machine-executable instructions 220. The machine-executable instructions enable the computational system 204 to perform various computational and data processing tasks as well as control other components of the medical system 200. The memory 210 is further shown as containing the analysis algorithm 100, the assessment algorithm 102, and the recommender algorithm 104. The memory 210 is further shown as containing the one or more planning magnetic resonance images 106 as well as the output of the analysis algorithm 116 and the output of the assessment algorithm 118. The memory 210 is further shown as containing a pulse sequence selection 222 or a stop acquisition command 224 that was output by the recommender algorithm 104. The various other data displayed in FIG. 1 may also be contained within the memory 210.

Figure 3:
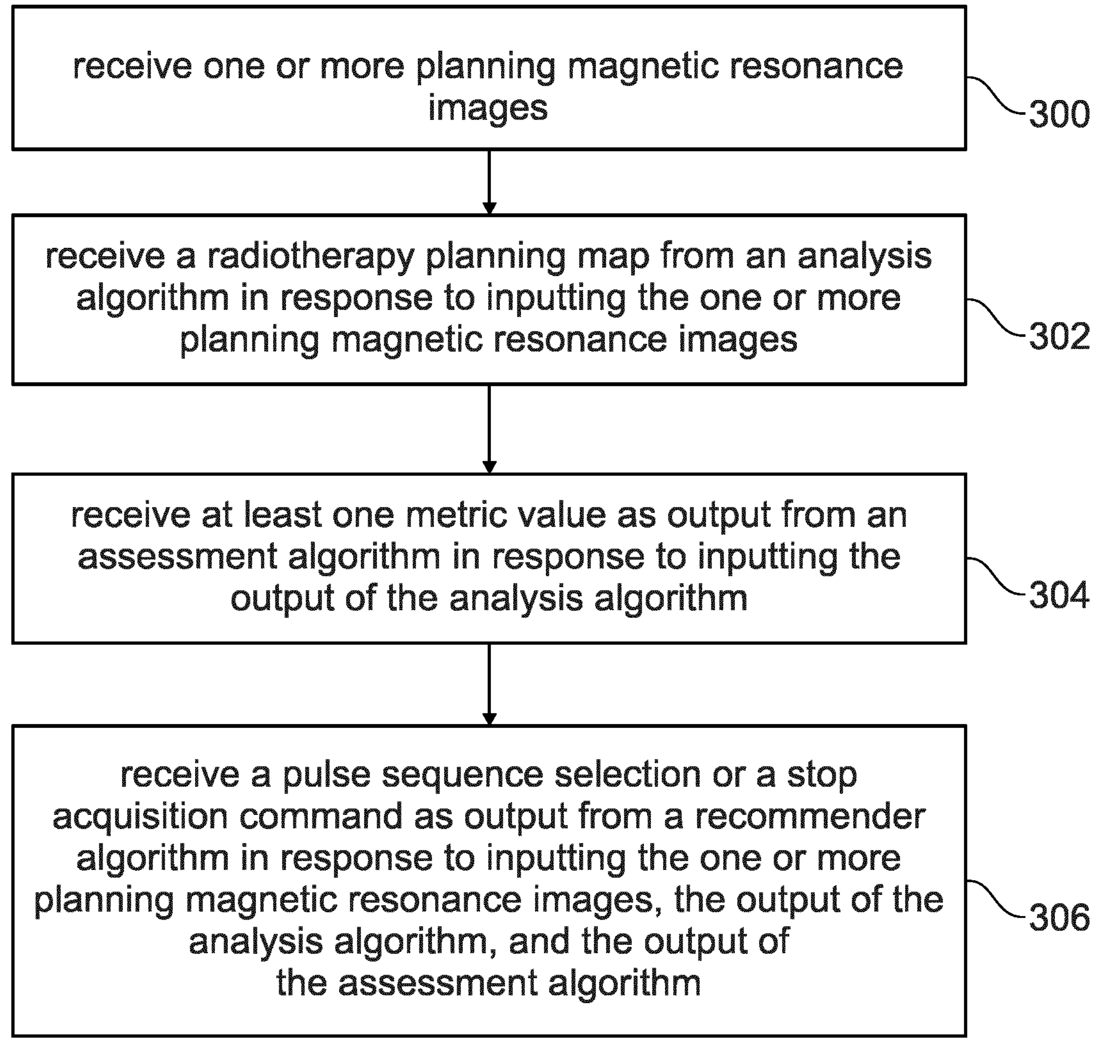
FIG. 3 shows a flow chart which illustrates a method of operating the medical system of FIG. 2.

FIG. 3 shows a flowchart which illustrates a method of operating the medical system 200 of FIG. 2. First, in step 300, one or more planning magnetic resonance images 106 are received. Next, in step 302, the radiotherapy planning map 116 is received from the analysis algorithm 100 in response to inputting the one or more planning magnetic resonance images 106 into the analysis algorithm 100. Then, in step 304, the at least one metric map 118 is received from the assessment algorithm 102 in response to inputting at least the output of the analysis algorithm 116. And finally, in step 306, the pulse sequence selection 222 or the stop acquisition command 224 is received from the recommender algorithm 104 in response to inputting the output of the analysis algorithm 116, the output of the assessment algorithm 118, and the one or more planning magnetic resonance images 106.

Figure 4:
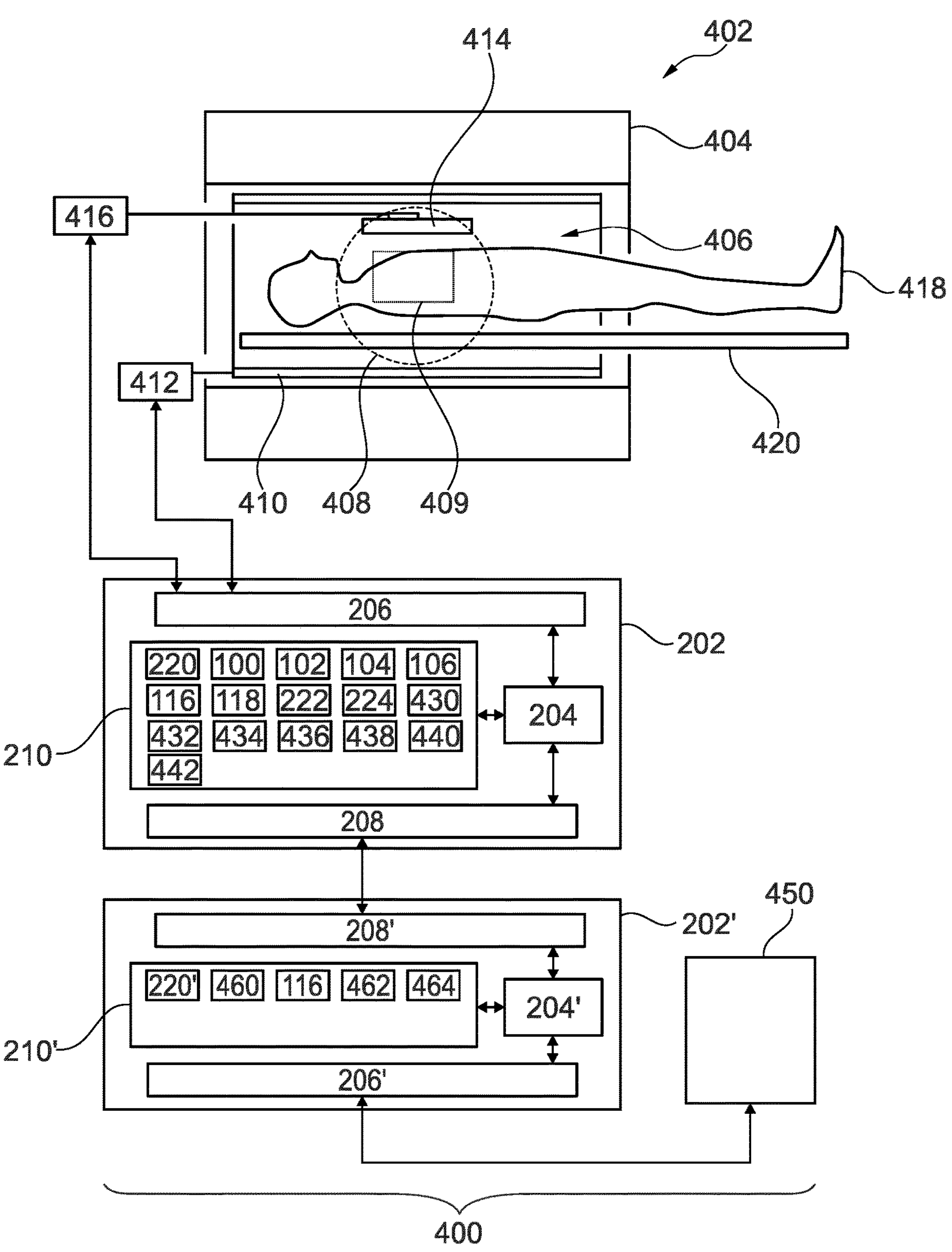
FIG. 4 illustrates a further example of a medical system.

FIG. 4 illustrates a further example of a medical system 400. The medical system 400 depicted in FIG. 4 is similar to the medical system 200 in FIG. 2 with several additional components. The medical system 400 is shown as additionally comprising a magnetic resonance imaging system 402 as well as an optional radiation therapy system 450 and an optional additional computer 202'.

The magnetic resonance imaging system 402 comprises a magnet 404. The magnet 404 is a superconducting cylindrical type magnet with a bore 406 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 406 of the cylindrical magnet 404 there is an imaging zone 408 where the magnetic field is strong and uniform enough to perform magnetic resonance imaging. A field of view 409 is shown within the imaging zone 408. The k-space data that is acquired typically acquired for the field of view 409. A subject 418 is shown as being supported by a subject support 420 such that at least a portion of the subject 418 is within the imaging zone 408 and the field of view 409. The region of interest may be identical with the field of view or the region of interest may be a sub volume of the field of view 409.

Within the bore 406 of the magnet there is also a set of magnetic field gradient coils 410 which is used for acquisition of preliminary k-space data to spatially encode magnetic spins within the imaging zone 408 of the magnet 404. The magnetic field gradient coils 410 connected to a magnetic field gradient coil power supply 412. The magnetic field gradient coils 410 are intended to be representative. Typically magnetic field gradient coils 410 contain three separate sets of coils for spatially encoding in three orthogonal spatial directions. A magnetic field gradient power supply supplies current to the magnetic field gradient coils. The current supplied to the magnetic field gradient coils 410 is controlled as a function of time and may be ramped or pulsed.

Adjacent to the imaging zone 408 is a radio-frequency coil 414 for manipulating the orientations of magnetic spins within the imaging zone 408 and for receiving radio transmissions from spins also within the imaging zone 408. The radio frequency antenna may contain multiple coil elements. The radio frequency antenna may also be referred to as a channel or antenna. The radio-frequency coil 414 is connected to a radio frequency transceiver 416. The radio-frequency coil 414 and radio frequency transceiver 416 may be replaced by separate transmit and receive coils and a separate transmitter and receiver. It is understood that the radio-frequency coil 414 and the radio frequency transceiver 416 are representative. The radio-frequency coil 414 is intended to also represent a dedicated transmit antenna and a dedicated receive antenna. Likewise the transceiver 416 may also represent a separate transmitter and receivers. The radio-frequency coil 414 may also have multiple receive/transmit elements and the radio frequency transceiver 416 may have multiple receive/transmit channels.

The transceiver 416 and the gradient controller 412 are shown as being connected to the hardware interface 206 of the computer system 202.

The memory 210 is further shown as containing initial pulse sequence commands 430. The memory 210 is further shown as containing initial k-space data 432 that was acquired by controlling the magnetic resonance imaging system 402 with the initial pulse sequence commands 430. The memory 210 is further shown as containing an initial planning magnetic resonance image 434 that was reconstructed from the initial k-space data 432. The memory 210 is further shown as containing a predetermined set of radiation therapy planning pulse sequence commands 436 then it is further shown as containing its subsequent pulse sequence commands 438 that were selected using the pulse sequence selection 222. The memory 210 is further shown as containing a subsequent planning magnetic resonance image 442 that was reconstructed from the subsequent k-space data 440.

The additional computer 202' is similar to the computer 202 and it comprises a computational system 204', a hardware interface 206', a network interface 208', and a memory 210'. The memory 210' is shown as containing machine-executable instructions 220' that also enable the computational system 204' to perform various data manipulation and computational tasks as well as control of the radiation therapy system 450. The memory 210' is further shown as containing a radiotherapy planning module 460 that receives a radiotherapy planning map 116 as input and also optionally a planning computed tomography image 462 as input. In response, the radiotherapy planning module 460 outputs radiotherapy control commands 464. These are the actual commands which are used by the radiation therapy system 450 to control and eradiate the subject 418. The features of the computer 200 and 202' may be combined. The radiation therapy system 450 may also be integrated with the magnetic resonance imaging system 402 or they may be separate apparatuses. But in some examples the radiotherapy system 450 may be guided by the magnetic resonance imaging system 402.

Figure 5:
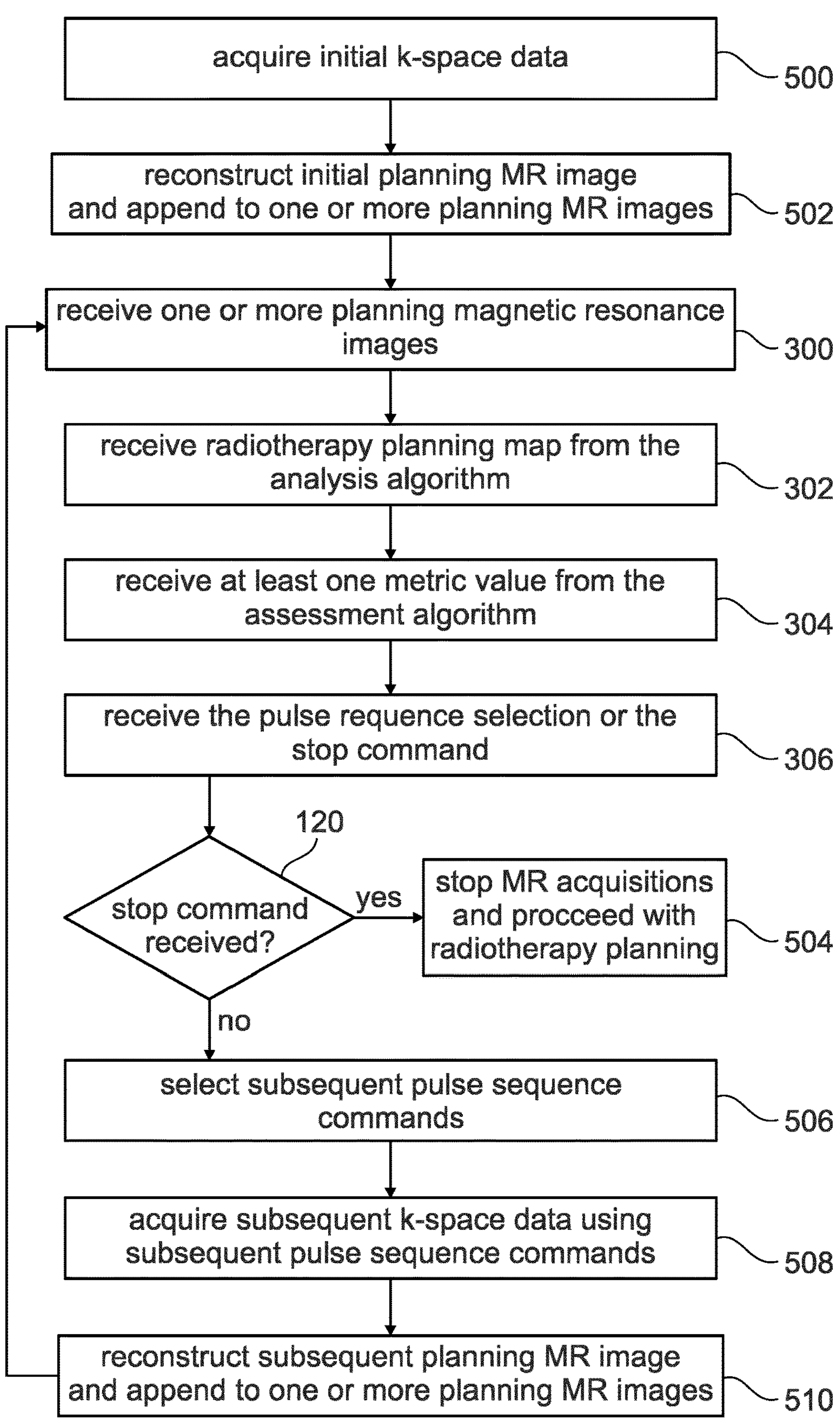
FIG. 5 shows a flow chart which illustrates a method of operating the medical system of FIG. 4.

FIG. 5 shows a flowchart which illustrates a method of operating the medical system 400 of FIG. 4. First, in step 500, the initial k-space data 432 is acquired by controlling the magnetic resonance imaging system 402 with the initial pulse sequence commands 430. Next, in step 502, the initial planning magnetic resonance image 434 is reconstructed from the initial k-space data 432. The initial planning magnetic resonance image 434 is appended to the one or more planning magnetic resonance images 106. In fact, in the first iteration the initial planning magnetic resonance image 434 may be identical with the one or more planning magnetic resonance images 106. Next the method proceeds to steps 300, 302, 304, and 306 as was illustrated in FIG. 3. After step 306 is performed, the method proceeds to step 120 which is a decision box: has the stop command been received. If the answer is yet, the method proceeds to box 504 and acquisitions by the magnetic resonance imaging system 402 are halted and the radiotherapy planning map 116 may be used for radiotherapy. In this case the components in the computer 202' are used to generate the radiotherapy control commands 464 to control the radiation therapy system 450. Returning to box 120, if the stop commands have not been received then the method proceeds to step 506. In this case, the subsequent pulse sequence commands 438 are selected from the predetermined set of radiation therapy planning pulse sequence commands 436 using the pulse sequence selection 222. Next, in step 508, the subsequent k-space data 440 is acquired by controlling the magnetic resonance imaging system with the subsequent pulse sequence commands 438. Next, in step 510, the subsequent planning magnetic resonance image 442 is reconstructed from the subsequent k-space data 440. The subsequent planning magnetic resonance image 442 is then appended to the one or more planning magnetic resonance images 106 and the method returns back to step 300. This process is repeated until the loop is for example performed a predetermined number of times or the stop command is received and the method ends with box 504.

Radiation Oncology is seeing a growth in the adoption of MRI for guidance, response assessment, and mainly for treatment planning. Its use is spreading to multiple anatomies: brain, pelvis, abdomen, head, head & neck, breast, thorax.

In a Radiation Therapy (RT) planning workflow using MR, e.g., the physicians currently acquire:

- a CT scan: information on electron density is required for dose simulation
- MR volume(s): MRI provides better contrasted tissues for the delineation of the target volumes and the organs at risk (OARs).

Various protocols have been proposed to tackle different anatomies. Standard MR sequences are usually axial/sagittal T1w and T2w, for registration with CT and target and OAR delineation. There is also an increasing use of T1w sequences with contrast agent, FLAIR, Dixon sequences, DWI, ADC maps, etc. Some of them address specific needs of the different anatomies, but most contrasts (one or more planning magnetic resonance images 106) are used to assist the physician during the delineation of the target and the OARs.

MRI data providing multiple contrasts corresponding to different acquisition sequences (predetermined set of radiation therapy planning pulse sequence commands 436) are useful for clinical practice, in particular for tumor and OARs segmentation. In this latter case, each contrast provides useful information which potentially increases the accuracy of the automated analysis. However, increasing the number of contrasts in hope of accuracy gains has several drawbacks:

- Since MRI sequences are performed sequentially, and since the duration of acquisition of each is in the order of one to several minutes, the acquisition of the totality of the multi-channel data can be long, causing problems in the data collection itself (registration of volumes in case the patient has changed position between sequences), or for the patient himself (as the experience of an MRI-scan is generally perceived as unpleasant). Depending on the targeted anatomy, the field of view and the clinical practice, the total acquisition time ranges from a couple of minutes to more than 30 minutes. While the gains may not be significant on short protocols, suppressing the need for just one MR sequence from a lengthy protocol of 4-5 sequences of 5 minutes each, would lead to a gain of 20-25% in total acquisition time.
- In case the analysis consists in manual segmentation performed by a clinician, the latter has to review many MR contrasts together, which can lengthen the segmentation process, either by requiring more time for review during the contouring and contouring approval phases, or by generating more feedback loops between these two workflow steps. As a consequence of the latter, examples can potentially reduce the time to treatment. Note that this argument is not limited to segmentation tasks, as other tasks (quantitative measurements, for example) can be time-consuming as well.
- In case the analysis task is performed in an automated manner, the amount of data can rapidly increase with the number of MR contrast volumes, and the algorithms may possibly scale accordingly.

There is therefore an interest for a process able to determine the optimal contrasts of an MRI volume for the clinical practice under consideration. This optimal number of channels would reduce both the time needed for acquisition and the time for processing the data.

Example may provide a process for acquiring multiple MR contrasts based on automated analysis coupled to MRI sequence recommendation.

The process may comprise one or more of the following features:

- An MRI equipment able to acquire MRI data under a plurality of MRI sequences (one or more planning magnetic resonance images 106),
- An automated analysis system (AAS or analysis algorithm 100), which takes as an input the previously acquired MRI sequences and outputs a clinically-relevant analysis of the MRI volume,
- A quality assessment system (QAS or assessment algorithm 102), which takes as inputs the previously acquired MRI sequences (one or more planning magnetic resonance images 106), and possibly other sources of information (e.g. volumes from other modalities such as a previously acquired CT scan or tomographic medical images 108) and outputs measures of the quality or the at least one metric map 118 of the output, or parts of the output, of the AAS, according to metrics relevant for the clinical application,
- A recommender system (recommender algorithm 104), which takes as an input the previously acquired MRI data (one or more planning magnetic resonance images 106), along with the results of the AAS and the QAS 102, and outputs a choice of recommendations (pulse sequence selection 222) regarding the next MRI sequence to be performed that would maximize the clinically-relevant metrics assessed by the QAS 102. This choice of recommendations can be visually presented to the operator of the MRI equipment for validation.

The presence of the quality assessment information from the QAS 102 allows the recommender system to evaluate the quality of the acquired data with respect to the clinical application and to recommend the appropriate MRI sequences.

In an example, the automated analysis system (AAS 100), the quality assessment system (QAS 102) and the recommender system 104 are pre-trained systems operating on the output of the MRI equipment.

In an example, the AAS 100 is previously trained on a specific task, and is able to output a prediction. For example, the analysis system can be, without being limited to, a Deep Learning based neural network taking multiple MRI contrasts as an input. The training of such networks is well known from the art.

In another example, the automated analysis system 100 takes as its input the MRI data resulting from all the previously acquired sequences. In this process, the quality assessed by the QAS is expected to increase with each new acquisition cycle.

In another example, the AAS 100 is an algorithm predicting a single- or multi-label, 2D or 3D segmentation. In another example, the AAS 100 is an algorithm predicting quantitative measurements such as lengths, areas, volumes, and so on. These two cases are merely examples and do not restrict the general purpose of the analysis system as considered.

In another example, the quality assessment system is previously trained and operates sequentially from predictions provided by the AAS 100.

In another example, the QAS 102 receives as additional inputs information from external sources such as, but not limited to, a previously acquired CT scan, segmentation maps from previous time points during treatment, etc.

In another example, the AAS 100 and the QAS 102 are combined into a single system 103 capable of doing both jointly. An example of this embodiment is a Deep Learning network performing single- or multi-label, 2D or 3D segmentation, using mechanisms such as Dropout layers to estimate uncertainty. In this case, the uncertainty in the segmentation result is considered as the QAS 102 output (the QAS 102 and the AAS 100 being one and the same), which future recommendations of additional MRI sequences aim to lower.

In another example, the automated recommender system 100 is trained using a plurality of multi-channel MRI volume samples along with the outputs of the AAS 100 and the QAS 102 as its inputs, and using known outputs regarding the best choice of MRI sequence. These outputs can be given for example by experts in the field. The automated recommender system 104 can, without being limited to, be a Deep Learning based neural network trained using well-known methods from the art.

In another example, the results of the recommender system 104 are presented visually to the operator of the MRI equipment for validation. In an alternative embodiment of the invention, both the results of the AAS 100 and the QAS 102, and the results of the recommender system 104 are presented visually to the operator.

In another example, the recommender system 104 is able to give information regarding the uncertainty of its prediction result, for example if multiple MRI sequences are recommended with similar rating or preference levels.

In another example, the recommender system 104 is able to tell if none of its available choices are recommended, or in other words whether the acquisition should be stopped (it issues a stop acquisition command 224).

To better illustrate a further example, an exemplary realization in the case of OARs delineation for RT planning is presented below:

- The AAS 100 and QAS 102 are a single system, namely a U-Net like neural network performing multi-label segmentation and using Dropout layers as a Bayesian approximation to estimate uncertainty on the label map.
- The recommender system 104 has been trained to recommend the next MR sequence to be acquired to achieve an optimal gain on the overall segmentation accuracy, i.e. metrics averaged on all the labels.
- An MR operator provides a protocol as a set of mandatory MR sequences to be acquired. He/she can also provide a set of additional MR sequences that could help delineating the OARs. Then the mandatory MR sequences are acquired and the AAS 100/QAS 102 analysis is performed on the MRI data acquired so far.
- In a first example, the recommender system decides that the quality of the contours is sufficient for the subsequent steps of RT planning, thus no additional MR sequence(s) are needed. The total acquisition time has been reduced by avoiding acquiring additional MR sequences.
- In a second example, the recommender system suggests acquiring a new MR sequence (from the initial list provided by the MR operator, or given prior knowledge acquired during the training phase) to improve the contours. In this case, the global time-to-treatment may have been reduced by improving the segmentation outcome, either by decreasing the number of manual corrections needed during contouring, or by reducing the number of feedback loops between contouring and contouring approval.

The Automated Analysis System (AAS 100) is discussed in greater detail:

- Inputs: n distinct images (the one or more planning magnetic resonance images 106) corresponding to the acquisition with distinct MRI pulse sequences.

- Outputs: a radiotherapy planning map 116. Examples are the segmentation of one or many relevant organs, the generation of a pseudo-CT map, the prediction of a dose plan, etc.
- Training: In the case of the segmentation, the AAS 100 can be implemented with (without being limited to) a deep learning system, in which the architecture of the neural network can be a U-Net, a U-Net++, or any similarly relevant architecture. The training is performed using a dataset of MRI images acquired with different pulse sequences on the same patient as inputs, coupled with corresponding ground-truth segmentations (obtained for example by the manual segmentation by a clinician).

This network (the AAS 100) may accommodate a varying number of MRI contrasts as its input. The technical solutions for doing so are well-known from the state of the art. This can include for example:

- Imposing on the input of the U-Net, U-Net++, or any similar network to have k distinct channels, so that these channels are simultaneously processed to output the segmentation. In the case an image corresponding to a given MRI pulse sequence is not present in the patient data, it can be set to zero (zero-padded at the channel level), indicating missing data. It is also well-known from the state-of-the-art how to deal with missing input channel(s).
- Having k distinct networks for each of the k MRI pulse sequences, each network outputting an intermediate result, these k intermediate results then being recombined to output the final segmentation. The recombination network can be chosen for example to be (without being limited to) a convolutional network, a recurrent network (using for example LSTMs, GRUs, or any similar neuron layers), a Transformer architecture, etc. The k distinct networks and the recombination network can be trained end-to-end.

The Quality Assessment System (QAS 102) is discussed in greater detail:

- Inputs: the result of the AAS+(optional) the distinct images corresponding to the acquisition with distinct MRI pulse sequences (one or more planning magnetic resonance images 106)+(optional) other sources of information (e.g. volumes from other modalities such as a previously acquired CT scan, the additional tomographic medical images 114).
- Outputs: measure of the quality of the output (or parts of) the AAS 100. This measure can be spatially localized: for example, it may be described as a heatmap image indicating the quality for different locations in the volume of the patient.
- Training: The QAS 102 does not necessarily need to be trained. For example, the quality of the AAS 100 output can be assessed by numerical methods, such as describing the contour smoothness, the histogram of deviations with respect to reference organs and segmentations, etc. Additionally, the QAS 102 can be implemented with (without being limited to) a deep learning system, in which the architecture of the neural network can be a U-Net, a U-Net++, or any similarly relevant architecture. In this case, the training is performed using a dataset of MRI images acquired with different pulse sequences on the same patient as inputs, coupled with ground-truth quality annotations as outputs.

It should be noted that the AAS 100 and the QAS 102 may be combined into one single unit 103. As an example of a possible mode of realization, a U-Net architecture (or any similar architecture) can be trained on MRI contrasts to provide segmentations of one (or many) organ(s). Using this trained neural network, techniques have been described to enhance the segmentation result with additional information such as the local uncertainty of the segmentation (for example, using Dropout layers). This local measure of uncertainty may be considered, for certain applications, as a local measure of quality.

The Recommender System 104 is discussed in greater detail:

- Inputs: the distinct images corresponding to the acquisition with distinct MRI pulse sequences+the results of the AAS 100 and the QAS 102+(optional) other sources of information (e.g. volumes from other modalities such as a previously acquired CT scan or one or more planning magnetic resonance images 106).
- Output: a listed choice (pulse sequence selection 222) of MRI pulse sequences (predetermined set of radiation therapy planning pulse sequence commands to be acquired 436), possibly sorted according to a given ranking measure. These MRI pulse sequences are a subset of the total, fixed, number N of available MRI pulse sequences. In practice, the set of N possible MRI pulse sequences is limited by the types of sequences the AAS 100 has been trained on i.e., the AAS 100 may be able to make use of these MRI pulse sequences.

Training: Assuming that the recommender system is implemented as a machine learning module, the supervised training can be performed in a number of ways (without being limited to these particular examples).

In one possible implementation, supervision comes from a clinician's input. The following data is available for each patient: a set of k distinct images corresponding to distinct MRI pulse sequences, along with any optional data such as described above. A clinician then manually assesses which MRI pulse sequences among the (N-k) remaining ones would be suitable to improve the results of the AAS, possibly ranking them. Alternatively, the clinician may select only one MRI pulse sequence as the next suitable candidate. In this case the recommender system is trained such that the output corresponds to one-hot encoded MRI pulse sequences. This can be trained with a categorical cross-entropy loss for example.

In another possible implementation, the ground-truth annotation by a clinician is not possible, and the supervision comes from pseudo-labels generated as follows. The following data is available for each patient: a set of N distinct images corresponding to distinct MRI pulse sequences, along with any optional data such as described above. In this case, the AA S+ QAS modules can be run offline on a subset S of k images of the N images in the patient data, then on (N-k) subsets S' comprising S plus one of the remaining N-k images. The (N-k) quality measures thus obtained then allows one to determine which one of the (N-k) MRI pulse sequence gives the best result, which determines the annotation on which to train the recommender system. Again, this can be one-hot encoded and trained as described above.

In addition to the details provided above, the Analysis algorithm 100 can be a region growing algorithm, a deformable shape model, a trained neural network, a trained random forest, and etc.

The assessment algorithm 102 can be a statistical method to measure the stability of the radiotherapy planning map (e.g., Monte-Carlo simulation), correlation of the results with saliency maps (e.g., with image gradients), fitness to statistical shape models (distance from an average model, PCA), fitness to statistical appearance models (texture analysis, reconstruction from dictionary).

The metric map 118 can be a map of numbers that measures the local uncertainty of the radiotherapy planning map, the fitness to the image contents or to some prior anatomical knowledge.

The Recommender algorithm 104 can be a decision tree, an expert system, a trained neural network, a trained random forest, etc.

The image merging algorithm can as describe above can be e.g. a statistical combination of intermediate radiotherapy planning maps (average, min, max, and etc.) or a trained neural network, a trained random forest, etc.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

REFERENCE SIGNS LIST

100 analysis algorithm (AAS)
102 assessment algorithm (QAS)
103 single or combined algorithm
104 recommender algorithm
106 one or more planning magnetic resonance images
108 tomographic medical images
110 additional tomographic medical images
112 further tomographic medical images
114 supplementary tomographic medical images
116 output of analysis algorithm (radiotherapy planning map)
118 output of assessment algorithm (at least one metric map)
120 stop command provided?
122 end acquisition of planning magnetic resonance images
124 select radiation therapy planning pulse
200 medical system
202 computer
202' computer
204 computational system
204' computational system
206 hardware interface
206' hardware interface
208 network interface
208 network interface
210 memory
210 memory
220 machine executable instructions
220' machine executable instructions
222 pulse sequence selection
224 stop acquisition command
300 receive the one or more planning magnetic resonance images
302 receive the radio therapy planning map from the analysis algorithm as output in response to inputting the one or more planning magnetic resonance images into the analysis algorithm
304 receive the at least one metric map as output from the assessment algorithm in response to inputting the output of the radio therapy planning map into the assessment algorithm
306 receive the pulse sequence selection or the stop acquisition command as output from the recommender algorithm in response to inputting the one or more planning magnetic resonance images, the output of the analysis algorithm, and the output of the assessment algorithm
400 medical system
402 magnetic resonance imaging system
404 magnet
406 bore of magnet
408 imaging zone
409 field of view
410 magnetic field gradient coils
412 magnetic field gradient coil power supply
414 radio-frequency coil
416 transceiver
418 subject
420 subject support
430 initial pulse sequence commands
432 initial k-space data
434 initial planning magnetic resonance image
436 predetermined set of radiation therapy planning pulse sequence commands
438 subsequent pulse sequence commands
440 subsequent k-space data
442 subseuqent planning magnetic resonance image
450 radiation therapy system
460 radiotheapy planning module
462 planning computed tomography image
464 radiotherapy control commands
500 acquire the initial k-space data;
502 reconstruct an initial planning magnetic resonance image from the initial k-space data
506 select subsequent pulse sequence commands from the predetermined set of radiation therapy planning pulse sequence commands using the pulse sequence selection
508 acquire subsequent k-space data by controlling the magnetic resonance imaging system with the subsequent pulse sequence commands
510 reconstruct a subsequent planning magnetic resonance image from the subsequent k-space data

The invention claimed is:

1. A medical system comprising:

a memory configured to store machine executable instructions, an analysis algorithm, an assessment algorithm, and a recommender algorithm; wherein the analysis algorithm is configured to output a radiotherapy planning map in response to receiving one or more planning magnetic resonance images descriptive of a region of interest of a subject;

wherein the assessment algorithm is configured to output at least one metric map descriptive of the radiotherapy planning map within the region of interest in response to receiving the output of the analysis algorithm;

wherein the recommender algorithm is configured to output either a pulse sequence selection or a stop acquisition command in response to receiving the one or more planning magnetic resonance images, the output of the analysis algorithm, and the output of the assessment algorithm as input; wherein the pulse sequence selection is a planning magnetic resonance imaging pulse sequence selection and a selection or ranking of a predetermined set of radiation therapy planning pulse sequence commands; and a computational system, wherein execution of the machine executable instructions causes the computational system to:

receive the one or more planning magnetic resonance images;

receive the radio therapy planning map from the analysis algorithm as output in response to inputting the one or more planning magnetic resonance images into the analysis algorithm;

receive the at least one metric map as output from the assessment algorithm in response to inputting the output of the radio therapy planning map into the assessment algorithm; and receive the pulse sequence selection or the stop acquisition command as output from the recommender algorithm in response to inputting the one or more planning magnetic resonance images, the output of the analysis algorithm, and the output of the assessment algorithm.

2. The medical system of claim 1, wherein the recommender algorithm is further configured to receive at least one additional tomographic medical image descriptive of the region of interest of the subject as input, wherein execution of the machine executable instructions causes the computational system to additionally input the at least one additional tomographic medical image into the recommender algorithm.

3. The medical system of claim 1, wherein the assessment algorithm is further configured to receive the one or more planning magnetic resonance images and/or receive at least one further tomographic medical image descriptive of the region of interest of the subject as input, wherein execution of the machine executable instructions further causes the computational system to additionally input the one or more planning magnetic resonance images and/or the at least one further tomographic medical image into the assessment algorithm.

4. The medical system of claim 1, wherein the analysis algorithm is further configured to receive at least one supplementary tomographic medical image descriptive of the region of interest of the subject as input, wherein execution of the machine executable instructions causes the computational system to additionally input the at least one supplementary tomographic medical image into the analysis algorithm.

5. The medical system of claim 1 wherein the analysis algorithm is configured to receive up to a predetermined maximum number of planning magnetic resonance images, wherein the analysis algorithm is configured to receive the one or more planning magnetic resonance images using any one the following algorithm architecture:

wherein the input of the analysis algorithm comprises a separate input channel for each of the planning magnetic resonance images; and wherein the analysis algorithm comprises an image processing algorithm configured for receiving each of the predetermined maximum number of planning magnetic resonance images individually and in response each outputting an intermediate radiotherapy planning map, wherein the analysis algorithm further comprises an image merging algorithm configured for receiving the intermediate radiotherapy planning map of each image processing algorithm and in response outputting the radiotherapy planning map.

6. The medical system of claim 1, wherein the analysis algorithm and the assessment algorithm are implemented as a single algorithm.

7. The medical system of claim 1, wherein the radiotherapy planning map comprises any one of the following: an organ segmentation, an identification of abnormal anatomical structures, a tumor segmentation, a pseudo computed tomography image, an electron density map, a radiotherapy dose plan, and combinations thereof.

8. The medical system of claim 1, wherein the analysis algorithm is any one of the following: a region growing algorithm, a deformable shape model, a trained neural network, a trained random forest, and a registration algorithm configured to register the one or more planning magnetic resonance images to an anatomical atlas.

9. The medical system of claim 1, wherein the assessment algorithm is any one of the following: a Monte-Carlo simulation configured for predicting the stability of the radiotherapy planning map, a model configured to measure a correlation in comparison with a saliency map, a principal components analysis model, an algorithm configured to measure a distance to an average model, a fitness to a statistical appearance model such as a texture analysis or a reconstruction from an archived model.

10. The medical system of claim 1, wherein the recommender algorithm is any one of the following: a decision tree algorithm, a trained recommender neural network, and a trained random forest algorithm.

11. The medical system of claim 1, wherein the medical system further comprises a magnetic resonance imaging system, wherein the memory further contains the predetermined set of radiation therapy planning pulse sequence commands, wherein the predetermined set of radiation therapy planning pulse sequence commands comprises initial pulse sequence commands, wherein execution of the machine executable instructions further causes the computational system to:

acquire initial k-space data by controlling the magnetic resonance imaging system with the initial pulse sequence commands;

reconstruct an initial planning magnetic resonance image from the initial k-space data, wherein the initial planning magnetic resonance image is added to the one or more planning magnetic resonance images;

wherein execution of the machine executable instructions further causes the computational system to repeatedly perform the following steps until receiving the stop command is received:

receive the radio therapy planning map from the analysis algorithm as output in response to inputting the one or more planning magnetic resonance images into the analysis algorithm;

receive the at least one metric map as output from the assessment algorithm in response to inputting the output of the radio therapy planning map into the assessment algorithm;

receive the pulse sequence selection or the stop acquisition command as output from the recommender algorithm in response to inputting the one or more planning magnetic resonance images, the output of the analysis algorithm, and the output of the assessment algorithm;

select subsequent pulse sequence commands from the predetermined set of radiation therapy planning pulse sequence commands using the pulse sequence selection;

acquire subsequent k-space data by controlling the magnetic resonance imaging system with the subsequent pulse sequence commands; and reconstruct a subsequent planning magnetic resonance image from the subsequent k-space data, wherein the subsequent planning magnetic resonance image is added to the one or more planning magnetic resonance images.

12. The medical system of claim 11, wherein the memory further contains a radiotherapy planning module configured to generate radio therapy control commands in response to receiving the radiotherapy planning map, wherein execution of the machine executable instructions further cause the computational system to receive the radiotherapy control commands from the radiotherapy planning module in response to inputting the radiotherapy planning map into the radiotherapy planning module.

13. The medical system of claim 12, wherein the radiotherapy planning map is further configured to receive a planning computed tomography image descriptive of the subject and the radiotherapy planning map as input, wherein the planning computed tomography image is a measured computed tomography image or a pseudo computed tomography image, wherein execution of the machine executable instructions further causes the computational system to receive the radiotherapy control commands from the radiotherapy planning module in response to inputting the radiotherapy planning map and the planning computed tomography image into the radiotherapy planning module.

14. A method of operating a medical system, wherein the method comprises:

receiving one or more planning magnetic resonance images descriptive of a region of interest of a subject;

receiving a radio therapy planning map from an analysis algorithm as output in response to inputting the one or more planning magnetic resonance images into the analysis algorithm, wherein the analysis algorithm is configured to output the radiotherapy planning map in response to receiving the one or more planning magnetic resonance images descriptive of the region of interest of the subject;

receiving at least one metric map as output from an assessment algorithm in response to inputting the output of the radio therapy planning map into the assessment algorithm, wherein the assessment algorithm is configured to output the at least one metric map descriptive of the radiotherapy planning map within the region of interest in response to receiving the output of the analysis algorithm; and receiving a pulse sequence selection or a stop acquisition command as output from a recommender algorithm in response to inputting the one or more planning magnetic resonance images, the output of the analysis algorithm, and the output of the assessment algorithm; wherein the recommender algorithm is configured to output either the pulse sequence selection or the stop acquisition command in response to receiving the one or more planning magnetic resonance images, the output of the analysis algorithm, and the output of the assessment algorithm as input; wherein the pulse sequence selection is a selection or ranking of a predetermined set of radiation therapy planning pulse sequence commands.

15. A computer program comprising machine executable instructions stored on a non-transitory computer readable medium, the computer program including: an analysis algorithm, an assessment algorithm, and a recommender algorithm; wherein the analysis algorithm is configured to output a radiotherapy planning map in response to receiving one or more planning magnetic resonance images descriptive of a region of interest of a subject; wherein the assessment algorithm is configured to output at least one metric map descriptive of the radiotherapy planning map within the region of interest in response to receiving the output of the analysis algorithm; wherein the recommender algorithm is configured to output either a pulse sequence selection or a stop acquisition command in response to receiving the one or more planning magnetic resonance images, the output of the analysis algorithm, and the output of the assessment algorithm as input; wherein the pulse sequence selection is a selection or ranking of a predetermined set of radiation therapy planning pulse sequence commands; wherein execution of the machine executable instructions causes the computational system to:

receive the one or more planning magnetic resonance images;

receive the radio therapy planning map from the analysis algorithm as output in response to inputting the one or more planning magnetic resonance images into the analysis algorithm;

receive the at least one metric map as output from the assessment algorithm in response to inputting the output of the radio therapy planning map into the assessment algorithm; and receive the pulse sequence selection or the stop acquisition command as output from the recommender algorithm in response to inputting the one or more planning magnetic resonance images, the output of the analysis algorithm, and the output of the assessment algorithm.

* * * * *